United States Patent [19]
Crawford et al.

[11] Patent Number: 6,107,057
[45] Date of Patent: Aug. 22, 2000

[54] PICHIA SECRETORY LEADER FOR PROTEIN EXPRESSION

[75] Inventors: Kenneth Crawford, Alameda; Isabel Zaror, Orinda; Robert J. Bishop, San Francisco; Michael A. Innis, Moraga, all of Calif.

[73] Assignee: Chiron Corporation, Emeryville, Calif.

[21] Appl. No.: 09/029,267

[22] PCT Filed: Sep. 25, 1996

[86] PCT No.: PCT/US96/15329

§ 371 Date: Feb. 24, 1998

§ 102(e) Date: Feb. 24, 1998

[87] PCT Pub. No.: WO97/12044

PCT Pub. Date: Apr. 3, 1997

Related U.S. Application Data

[60] Provisional application No. 60/004,264, Sep. 25, 1995, and provisional application No. 60/004,327, Sep. 26, 1995.

[51] Int. Cl.[7] .............................. C12P 21/00; C12N 5/10; C12N 1/11; C12N 15/31
[52] U.S. Cl. ................ 435/69.1; 435/91.41; 435/254.11; 435/255.5; 435/254.2; 435/254.21; 435/254.23; 435/252.3; 435/348; 435/349; 435/325; 536/24.1
[58] Field of Search ................ 435/69.1, 91.41, 435/254.11, 255.5, 254.2, 254.21, 254.23, 252.3, 348, 349, 325; 536/24.1

[56] References Cited

U.S. PATENT DOCUMENTS

| 5,324,639 | 6/1994 | Brierley et al. | 435/69.4 |
|---|---|---|---|
| 5,330,901 | 7/1994 | Prevatt et al. | 435/69.6 |

FOREIGN PATENT DOCUMENTS

| 0 256 421 A2 | 4/1987 | European Pat. Off. . |
|---|---|---|
| 0 438 200 A1 | 1/1991 | European Pat. Off. . |
| WO 97/12044 | 4/1997 | WIPO . |

OTHER PUBLICATIONS

Bolen et al. Isolation and sequence analysis of a gene from the linear DNA plasmid pPac1–2 of *Pichia acaciae* that shows similarity to a killer toxin gene of *Kluyveromyces lactis*. Yeast vol. 10 pp. 403–414, 1994.

von Heijne The signal peptide. J. Membrane Biology vol. 115 pp. 195–201, 1990.

Koutz et al., "Structural Comparison of the *Pichia pastoris* Alcohol Oxidase Genes", *Yeast* 5:167–177 (1989).

Cregg et al., "Functional Characterization of the Two Alcohol Oxidase Genes from the Yeast *Pichia pastoris*", *Molecular and Cellular Biology*, vol. 9, No. 3, pp. 1316–1323 (Mar., 1989).

Tschopp et al., "Expression of lacZ gene from Two Methanol–Regulated Promoters in *Pichia pastoris*", *Nucleic Acids Research*, vol. 15, No. 9, pp. 3859–3876 (1987).

Sreekrishna et al., "Invertase gene (SUC2) of *Saccharomyces cerevisiae* as a Dominant Marker for Transformation of *Pichia pastoris*", *Gene*, 59:115–125 (1987).

Cregg et al., "*Pichia pastoris* as a Host System for Transformations", *Molecular and Cellular Biology*, vol. 5, No. 12, pp. 3376–3385 (Dec. 1985).

Clare et al., "Production of Mouse Epidermal Growth Factor in Yeast: High–Level Secretion Using *Pichia pastoris* Strains Containing Multiple Gene Copies", *Gene*, 105:205–212 (1991).

Clare et al., "High–Level Expression of Tetanus Toxin Fragment C in *Pichia pastoris* Strains Containing Multiple Tandem Integrations of the Gene", *Bio/Technology*, 9:455–460 (May 1991).

Cregg et al., "Use of Site–Specific Recombination to Regenerate Selectable Markers", *Mol Gen Genet*, 219:320–323 (1989).

Sreekrishna et al., "High–Level Expression, Purification, and Characterization of Recombinant Human Tumor Necrosis Factor Synthesized in the Methylotrophic Yeast *Pichia pastoris*", *Biochemistry*, 28:4117–4125 (1989).

Tschopp et al., "High–Level Secretion of Glycosylated Invertase in the Methylotrophic Yeast, *Pichia pastoris*", *Bio/Technology*, 5:1305–1308 (Dec. 1987).

*Primary Examiner*—John S. Brusca
*Attorney, Agent, or Firm*—W. Murray Spruill; Joseph H. Guth; Robert P. Blackburn

[57] ABSTRACT

Polynucleotides, vectors, and host cells comprising a polynucleotide having a fragment of a leader sequence and a second nucleotide sequence that encodes a polypeptide heterologous to the leader sequence, wherein the leader sequence fragment is sufficient for secretion and comprises an amino acid sequence that comprises at least about 70% sequence identity to the leader sequence of *Pichia acaciae* killer toxin, wherein the heterologous polypeptide is not naturally contiguous to the leader sequence, and wherein upon expression of the polynucleotide molecule in a host cell suitable for expression thereof, the heterologous polypeptide is produced that is free of additional N-terminal amino acids.

29 Claims, 1 Drawing Sheet

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 1716 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 153..1625
      (D) OTHER INFORMATION: /codon_start= 153

(xi) SEQUENCE DESCRIPTION: SEQ ID NO:1:

```
AAAAGCATTA TGTTTTGAGG ACACAACCAA CCCCCACCCC ACCCCTCATT TCTTTGACCT      60

GCATATTAAT ATTGTTGTGA ATCTTGGCAT TACTTATTTT TTATTATGGG AGCGTTCTTC     120

ATATTTGAAT TTTTATTTTT GAAGCAATAA ATATGTTAAT TATAGTCTTA TTATTTTTAG     180

CTACTTTAGC TAATTCCCTC GATTGTAGCG GAGATGTATT TTTTGGATAT ACTAGAGGAG     240

ACAAAACAGA TGTTCATAAA AGTCAAGCAT TAACAGCGGT TAAAAATATT AAAAGATGGC     300

TTGGAAGTTT TGAAACAAGA CAGTCCTTTA AAGTAATAGA AGGTGATATT GCTGGTTTTG     360

CTTGGGTAGG TAGTTATATT AAGAACTCTG ATTTTGTTGA TAATGTAATT GAGATTATGT     420

ATAATGAAGT AAATAAAAAT GGTATACCAG TTGAACTTTA TATTGAGAAT ATCGTTGATA     480

ACGAGCCAGG TAAATCTTTT GGTTTTATTC TTAATTCTCA TAAAAACTTA GAAAATGCTC     540

AAAAAGCAGT TAAAAACTGG AGTACTGGGG TTAAGTATAA TGTTTATGAA GGTAATAAGA     600

TTTATAAAGA TCATTCCGTT TGTTATTTAG ATGAGTCTAA GAAAAAGCCA GAAGCTAACG     660

ATAAGGAAGC AGGTGAATGT TATTATACAA GACTAGGAGA TAATTCTAAT CCCTATACTC     720

AAGTTAAAAC TCCTAAGCCA TATTTAGATG TATTCAATTC TAATAATTTA ACTAAAATAG     780

TTAGTGGTGA AGCTTTTTGT TATTCTGAGG GCAGTTTACC TGATGTGGGT ATATGTGTTC     840

CTATTAAGTC TAATATGGAT TTTAAATATT ATAATAAATC ACCTAAACAA GATCTGGATA     900
```

-continued

```
AACAGAAAGT AATTAACGCT TTAAATACTT TAAGTAAAAA TTTTACTGAA TCTGAAAATC      960

GTCAATCTTT TATTTATCAA AAAGATAATA TAGTGGGCTA TATGTGGTTA GGTCAAAGAA     1020

TAAATAATAC TGAAAATTTG TTTAATTCAT TAACAAATGA GGTAACTAAA AATGGAGTTC     1080

CAGACCATTT TTATTATGAA TATGCTAAAA ATGATCCTAT GATACAAATA GGTATTTTTA     1140

TTAATAAACA AGGTAATGTA GATTTAGCTA ACAGGTAGG TAAAGTTTGG TCTACTGGTA      1200

AACAATTTAA TAATATTACT GGTAAAAAGT CGATTAGTAC TAGTTTTTGT ATATTAGATA     1260

ATAAAGAAAA AAGAGGATTT ACTAATGATT ATAGTGTTGG ACAATGTTTA AACTTTACTT     1320

ATGAAGAAAA TGTAAATGTA GGATTAACTG ATGAAATTCT TGTTGAATAT AATCCTGGTT     1380

TTTATAGTGC TAATTATGGT GACACTTTAT GTAAGAGTAT TGGTTATCCT CCTTCTAATA     1440

AACCTATAAA GGATTATTGT AAGTTTTATA TTGTACAAGA AGATGATACT TGTGTTAGTA     1500

TAGCTTCTAA ATATCCAGGA TTAACCGAAC AAGATATAAT TGATTATAAT TCAAAGAACG     1560

GTGACTTTTA TGGATGTTTT AATCTATGGG AAGGTGATAA GATTTGTATA TCTAAACCTT     1620

ACATGTAATA CTTTTGATTT TACTGTCAGA GTTACTATTG TCATTAATAG TATTAAACTT     1680

CTTATTTTCA GTGAATTCTA TTAATTTTGC GTGATC                               1716

(2) INFORMATION FOR SEQ ID NO:2:

(i) SEQUENCE CHARACTERISTICS:
        (A) LENGTH: 491 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Leu Ile Ile Val Leu Leu Phe Leu Ala Thr Leu Ala Asn Ser Leu
    1               5                   10                  15

Asp Cys Ser Gly Asp Val Phe Phe Gly Tyr Thr Arg Gly Asp Lys Thr
                20                  25                  30

Asp Val His Lys Ser Gln Ala Leu Thr Ala Val Lys Asn Ile Lys Arg
            35                  40                  45

Trp Leu Gly Ser Phe Glu Thr Arg Gln Ser Phe Lys Val Ile Glu Gly
        50                  55                  60

Asp Ile Ala Gly Phe Ala Trp Val Gly Ser Tyr Ile Lys Asn Ser Asp
    65                  70                  75                  80

Phe Val Asp Asn Val Ile Glu Ile Met Tyr Asn Glu Val Asn Lys Asn
                    85                  90                  95

Gly Ile Pro Val Glu Leu Tyr Ile Glu Asn Ile Val Asp Asn Glu Pro
                100                 105                 110

Gly Lys Ser Phe Gly Phe Ile Leu Asn Ser His Lys Asn Leu Glu Asn
                115                 120                 125

Ala Gln Lys Ala Val Lys Asn Trp Ser Thr Gly Val Lys Tyr Asn Val
            130                 135                 140

Tyr Glu Gly Asn Lys Ile Tyr Lys Asp His Ser Val Cys Tyr Leu Asp
    145                 150                 155                 160

Glu Ser Lys Lys Lys Pro Glu Ala Asn Asp Lys Glu Ala Gly Glu Cys
                    165                 170                 175

Tyr Tyr Thr Arg Leu Gly Asp Asn Ser Asn Pro Tyr Thr Gln Val Lys
                180                 185                 190

Thr Pro Lys Pro Tyr Leu Asp Val Phe Asn Ser Asn Asn Leu Thr Lys
```

```
                    195                 200                 205
    Ile Val Ser Gly Glu Ala Phe Cys Tyr Ser Glu Gly Ser Leu Pro Asp
            210                 215                 220
    Val Gly Ile Cys Val Pro Ile Lys Ser Asn Met Asp Phe Lys Tyr Tyr
    225                 230                 235                 240
    Asn Lys Ser Pro Lys Gln Asp Leu Asp Lys Gln Lys Val Ile Asn Ala
                    245                 250                 255
    Leu Asn Thr Leu Ser Lys Asn Phe Thr Glu Ser Glu Asn Arg Gln Ser
                260                 265                 270
    Phe Ile Tyr Gln Lys Asp Asn Ile Val Gly Tyr Met Trp Leu Gly Gln
                275                 280                 285
    Arg Ile Asn Asn Thr Glu Asn Leu Phe Asn Ser Leu Thr Asn Glu Val
    290                 295                 300
    Thr Lys Asn Gly Val Pro Asp His Phe Tyr Glu Tyr Ala Lys Asn
    305                 310                 315                 320
    Asp Pro Met Ile Gln Ile Gly Ile Phe Ile Asn Lys Gln Gly Asn Val
                    325                 330                 335
    Asp Leu Ala Lys Gln Val Gly Lys Val Trp Ser Thr Gly Lys Gln Phe
                340                 345                 350
    Asn Asn Ile Thr Gly Lys Lys Ser Ile Ser Thr Ser Phe Cys Ile Leu
                355                 360                 365
    Asp Asn Lys Glu Lys Arg Gly Phe Thr Asn Asp Tyr Ser Val Gly Gln
    370                 375                 380
    Cys Leu Asn Phe Thr Tyr Glu Glu Asn Val Asn Val Gly Leu Thr Asp
    385                 390                 395                 400
    Glu Ile Leu Val Glu Tyr Asn Pro Gly Phe Tyr Ser Ala Asn Tyr Gly
                    405                 410                 415
    Asp Thr Leu Cys Lys Ser Ile Gly Tyr Pro Pro Ser Asn Lys Pro Ile
                    420                 425                 430
    Lys Asp Tyr Cys Lys Phe Tyr Ile Val Gln Glu Asp Thr Cys Val
                435                 440                 445
    Ser Ile Ala Ser Lys Tyr Pro Gly Leu Thr Glu Gln Asp Ile Ile Asp
            450                 455                 460
    Tyr Asn Ser Lys Asn Gly Asp Phe Tyr Gly Cys Phe Asn Leu Trp Glu
    465                 470                 475                 480
    Gly Asp Lys Ile Cys Ile Ser Lys Pro Tyr Met
                    485                 490

(2) INFORMATION FOR SEQ ID NO:3:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:3:

AATTCATGTT AATTATAGTC TTATTATTTT TAGCTACTTT AGCTAATTCC CTCGATTGTA      60

GCGGA                                                                 65

(2) INFORMATION FOR SEQ ID NO:4:

(i) SEQUENCE CHARACTERISTICS:
        (A) LENGTH: 48 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:4:

GATGTATTTT TTGGATATAC TAGAGGAGAC AAAACAGATG TTCATAAA                48

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:5:

AGTCAAGCAT TAACAGCGGT TAAAAATATT AAACG                              35

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(ix) FEATURE:
        (A) NAME/KEY: misc_feature
        (B) LOCATION: 1
        (D) OTHER INFORMATION: /product= "5' Phosphate"

(xi) SEQUENCE DESCRIPTION: SEQ ID NO:6:

TAAAGTAGCT AAAAATAATA AGACTATAAT TAACATG                            37

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(ix) FEATURE:
        (A) NAME/KEY: misc_feature
        (B) LOCATION: 1
        (D) OTHER INFORMATION: /product= "5' phosphate"

(xi) SEQUENCE DESCRIPTION: SEQ ID NO:7:

TCTAGTATAT CCAAAAAATA CATCTCCGCT ACAATCGAGG GAATTAGC                48

(2) INFORMATION FOR SEQ ID NO:8:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "Synthetic"

(ix) FEATURE:
            (A) NAME/KEY: misc_feature
            (B) LOCATION: 1
            (D) OTHER INFORMATION: /product= "5' phosphate"

(xi) SEQUENCE DESCRIPTION: SEQ ID NO:8:

CATGCGTTTA ATATTTTTAA CCGCTGTTAA TGCTTGACTT TTATGAACAT CTGTTTTGTC     60

TCC                                                                 63

(2) INFORMATION FOR SEQ ID NO:9:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:9:

CGCGAATTCG ACAGAATGTT AATTATAGTC TTATTATTTT TAGC                     44

(2) INFORMATION FOR SEQ ID NO:10:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:10:

CGTCTCCGGT CCTCTTTTAA TATTTTTAAC CGCTGTTAAT GC                       42

(2) INFORMATION FOR SEQ ID NO:11:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:11:

CGCGAATTCG GTTCCTTATC AAGCTGACTT G                                   31

(2) INFORMATION FOR SEQ ID NO:12:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:12:

GTTAAAAATA TTAAAAGAGG ACCGGAGACG CTCTGCGGG                           39

(2) INFORMATION FOR SEQ ID NO:13:

(i) SEQUENCE CHARACTERISTICS:
            (A) LENGTH: 390 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:13:

CGCGAATTCG ACAGAATGTT AATTATAGTC TTATTATTTT TAGCTACTTT AGCTAATTCC      60

CTCGATTGTA GCGGAGATGT ATTTTTTGGA TATACTAGAG GAGACAAAAC AGATGTTCAT     120

AAAAGTCAAG CATTAACAGC GGTTAAAAAT ATTAAAAGAG GACCGGAGAC GCTCTGCGGG     180

GCTGAGCTCG TGGATGCTCT GCAGTTCGTG TGTGGAGACA GGGGCTTTTA TTTCAACAAG     240

CCCACAGGGT ATGGCTCCAG CAGTCGACGG GCGCCTCAGA CAGGCATCGT GGATGAGTGC     300

TGCTTCCGGA GCTGTGATCT AAGGAGGCTC GAGATGTATT GCGCACCCCT CAAGCCTGCC     360

AAGTCAGCTT GATAAGGAAC CGAATTCCGC                                     390

(2) INFORMATION FOR SEQ ID NO:14:

(i) SEQUENCE CHARACTERISTICS:
            (A) LENGTH: 118 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:14:

Met Leu Ile Ile Val Leu Leu Phe Leu Ala Thr Leu Ala Asn Ser Leu
       1               5                   10                  15

Asp Cys Ser Gly Asp Val Phe Phe Gly Tyr Thr Arg Gly Asp Lys Thr
                   20                  25                  30

Asp Val His Lys Ser Gln Ala Leu Thr Ala Val Lys Asn Ile Lys Arg
               35                  40                  45

Gly Pro Glu Thr Leu Cys Gly Ala Glu Leu Val Asp Ala Leu Gln Phe
       50                  55                  60

Val Cys Gly Asp Arg Gly Phe Tyr Phe Asn Lys Pro Thr Gly Tyr Gly
       65                  70                  75                  80

Ser Ser Ser Arg Arg Ala Pro Gln Thr Gly Ile Val Asp Glu Cys Cys
                       85                  90                  95

Phe Arg Ser Cys Asp Leu Arg Arg Leu Glu Met Tyr Cys Ala Pro Leu
                       100                 105                 110

Lys Pro Ala Lys Ser Ala
                   115

(2) INFORMATION FOR SEQ ID NO:15:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Gly Thr Glu Phe Arg
       1               5

(2) INFORMATION FOR SEQ ID NO:16:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GAATTCCCCT TAGACATGAC TGTTCCTCAG TTCAAGTTGG GCACTTACGA GAAGACCGGT      60

CTTGCTAGAT TCTAATCAAG AGGATGTCAG AATGCCATTT GCCTGAGAGA TGCAGGCTTC     120

ATTTTTGATA CTTTTTTATT TGTAACCTAT ATAGTATAGG ATTTTTTTTG TCATTTTGTT     180

TCCTTCTCGT ACGAGCTTGC TCCTGATCAG CCTATCTCGC AGCTGATGAA TATCTGTGGT     240

AGGGGTTTGG GAAAATCATT CGAGTTTGAT GTTTTTCTTG GTATTTCCCA CTCCTCTTCA     300

GAGTACAGAA GATTAAGTGA GACGTTCGTT TGTGCAAGCT T                        341
```

(2) INFORMATION FOR SEQ ID NO:17:

(i) SEQUENCE CHARACTERISTICS:
        (A) LENGTH: 163 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
TCGAGATAAG CTGGGGGACA TTCGCGAAAA TGAAACAAGT CGGCTGTTAT AGTATATTTA      60

TTATAATATT GAAAGATCTC AAAAGACTAC TTATTTTTGA ATGAACCAAG TATGAAATCA     120

ACCTATTTGG GGTTGACCAA AATAAGTAAA TATTAATTGT CGA                      163
```

(2) INFORMATION FOR SEQ ID NO:18:

(i) SEQUENCE CHARACTERISTICS:
        (A) LENGTH: 1018 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
AAGCTGACTC ATGTTGGTAT TGTGAAATAG ACGCAGATCG GGAACACTGA AAAATAACAG      60

TTATTATTCG AGATCTAACA TCCAAAGACG AAAGGTTGAA TGAAACCTTT TTGCCATCCG     120

ACATCCACAG GTCCATTCTC ACACATAAGT GCCAAACGCA ACAGGAGGGG ATACACTAGC     180

AGCAGACCGT TGCAAACGCA GGACCTCCAC TCCTCTTCTC CTCAACACCA CTTTTGCCAT     240

CGAAAAACCA GCCCAGTTAT TGGGCTTGAT TGGAGCTCGC TCATTCCAAT TCCTTCTATT     300

AGGCTACTAA CACCATGACT TTATTAGCCT GTCTATCCTG GCCCCCCTGG CGAGGTTCAT     360

GTTTGTTTAT TTCCGAATGC AACAAGCTCC GCATTACACC CGAACATCAC TCCAGATGAG     420

GGCTTTCTGA GTGTGGGGTC AAATAGTTTC ATGTTCCCCA AATGGCCCAA AACTGACAGT     480

TTAAACGCTG TCTTGGAACC TAATATGACA AAAGCGTGAT CTCATCCAAG ATGAACTAAG     540

TTTTGGTTCG TTGAAATGCT AACGGCCAGT TGGTCAAAAA GAAACTTCCA AAAGTCGGCA     600

TACCGTTTGT CTTGTTTGGT ATTGATTGAC GAATGCTCAA AAATAATCTC ATTAATGCTT     660
```

```
AGCGCAGTCT CTCTATCGCT TCTGAACCCC GGTGCACCTG TGCCGAAACG CAAATGGGGA    720

AACACCCGCT TTTTGGATGA TTATGCATTG TCTCCACATT GTATGCTTCC AAGATTCTGG    780

TGGGAATACT GCTGATAGCC TAACGTTCAT GATCAAAATT TAACTGTTCT AACCCCTACT    840

TGACAGCAAT ATATAAACAG AAGGAAGCTG CCCTGTCTTA AACCTTTTTT TTTATCATCA    900

TTATTAGCTT ACTTTCATAA TTGCGACTGG TTCCAATTGA CAAGCTTTTG ATTTTAACGA    960

CTTTTAACGA CAACTTGAGA AGATCAAAAA ACAACTAATT ATTCGAAACG AGGAATTC    1018

(2) INFORMATION FOR SEQ ID NO:19:

(i) SEQUENCE CHARACTERISTICS:
        (A) LENGTH: 2659 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGATCTCCTG ATGACTGACT CACTGATAAT AAAAATACGG CTTCAGAATT TCTCAAGACT     60

ACACTCACTG TCCGACTTCA AGTATGACAT TTCCCTTGCT ACCTGCATAC GCAAGTGTTG    120

CAGAGTTTGA TAATTCCTTG AGTTTGGTAG GAAAAGCCGT GTTTCCCTAT GCTGCTGACC    180

AGCTGCACAA CCTGATCAAG TTCACTCAAT CGACTGAGCT TCAAGTTAAT GTGCAAGTTG    240

AGTCATCCGT TACAGAGGAC CAATTTGAGG AGCTGATCGA CAACTTGCTC AAGTTGTACA    300

ATAATGGTAT CAATGAAGTG ATTTTGGACC TAGATTTGGC AGAAAGAGTT GTCCAAAGGA    360

TGATCCCAGG CGCTAGGGTT ATCTATAGGA CCCTGGTTGA TAAAGTTGCA TCCTTGCCCG    420

CTAATGCTAG TATCGCTGTG CCTTTTTCTT CTCCACTGGG CGATTTGAAA AGTTTCACTA    480

ATGGCGGTAG TAGAACTGTT TATGCTTTTT CTGAGACCGC AAAGTTGGTA GATGTGACTT    540

CCACTGTTGC TTCTGGTATA ATCCCCATTA TTGATGCTCG GCAATTGACT ACTGAATACG    600

AACTTTCTGA AGATGTCAAA AAGTTCCCTG TCAGTGAAAT TTTGTTGGCG TCTTTGACTA    660

CTGACCGCCC CGATGGTCTA TTCACTACTT TGGTGGCTGA CTCTTCTAAT TACTCGTTGG    720

GCCTGGTGTA CTCGTCCAAA AAGTCTATTC CGGAGGCTAT AAGGACACAA ACTGGAGTCT    780

ACCAATCTCG TCGTCACGGT TTGTGGTATA AAGGTGCTAC ATCGGAGCA ACTCAAAAGT    840

TGCTGGGTAT CGAATTGGAT TGTGATGGAG ACTGCTTGAA ATTTGTGGTT GAACAAACAG    900

GTGTTGGTTT CTGTCACTTG AACGCACTT CCTGTTTTGG CCAATCAAAG GGTCTTAGAG    960

CCATGGAAGC CACCTTGTGG GATCGTAAGA GCAATGCTCC AGAAGGTTCT TATACCAAAC   1020

GGTTATTTGA CGACGAAGTT TGTTGAACG CTAAAATTAG GGAGGAAGCT GATGAACTTG   1080

CAGAAGCTAA ATCCAAGGAA GATATAGCCT GGGAATGTGC TGACTTATTT TATTTTGCAT   1140

TAGTTAGATG TGCCAAGTAC GGTGTGACGT TGGACGAGGT GGAGAGAAAC CTGGATATGA   1200

AGTCCCTAAA GGTCACTAGA AGGAAAGGAG ATGCCAAGCC AGGATACACC AAGGAACAAC   1260

CTAAAGAAGA ATCCAAACCT AAAGAAGTCC CTTCTGAAGG TCGTATTGAA TTGTGCAAAA   1320

TTGACGTTTC TAAGGCCTCC TCACAAGAAA TTGAAGATGC CCTTCGTCGT CCTATCCAGA   1380

AAACGGAACA GATTATGGAA TTAGTCAAAC CAATTGTCGA CAATGTTCGT CAAAATGGTG   1440

ACAAAGCCCT TTTAGAACTA ACTGCCAAGT TGATGGAGT CGCTTTGAAG ACACCTGTGT   1500

TAGAAGCTCC TTTCCCAGAG GAACTTATGC AATTGCCAGA TAACGTTAAG AGAGCCATTG   1560

ATCTCTCTAT AGATAACGTC AGGAAATTCC ATGAAGCTCA ACTAACGGAG ACGTTGCAAG   1620
```

-continued

```
TTGAGACTTG CCCTGGTGTA GTCTGCTCTC GTTTTGCAAG ACCTATTGAG AAAGTTGGCC    1680

TCTATATTCC TGGTGGAACC GCAATTCTGC CTTCCACTTC CCTGATGCTG GGTGTTCCTG    1740

CCAAAGTTGC TGGTTGCAAA GAAATTGTTT TTGCATCTCC ACCTAAGAAG GATGGTACCC    1800

TTACCCCAGA AGTCATCTAC GTTGCCCACA AGGTTGGTGC TAAGTGTATC GTGCTAGCAG    1860

GAGGCGCCCA GGCAGTAGCT GCTATGGCTT ACGGAACAGA AACTGTTCCT AAGTGTGACA    1920

AAATATTTGG TCCAGGAAAC CAGTTCGTTA CTGCTGCCAA GATGATGGTT CAAAATGACA    1980

CATCAGCCCT GTGTAGTATT GACATGCCTG CTGGGCCTTC TGAAGTTCTA GTTATTGCTG    2040

ATAAATACGC TGATCCAGAT TTCGTTGCCT CAGACCTTCT GTCTCAAGCT GAACATGGTA    2100

TTGATTCCCA GGTGATTCTG TTGGCTGTCG ATATGACAGA CAAGGAGCTT GCCAGAATTG    2160

AAGATGCTGT TCACAACCAA GCTGTGCAGT TGCCAAGGGT TGAAATTGTA CGCAAGTGTA    2220

TTGCACACTC TACAACCCTA TCGGTTGCAA CCTACGAGCA GGCTTTGGAA ATGTCCAATC    2280

AGTACGCTCC TGAACACTTG ATCCTGCAAA TCGAGAATGC TTCTTCTTAT GTTGATCAAG    2340

TACAACACGC TGGATCTGTG TTTGTTGGTG CCTACTCTCC AGAGAGTTGT GGAGATTACT    2400

CCTCCGGTAC CAACCACACT TTGCCAACGT ACGGATATGC CCGTCAATAC AGCGGAGTTA    2460

ACACTGCAAC CTTCCAGAAG TTCATCACTT CACAAGACGT AACTCCTGAG GGACTGAAAC    2520

ATATTGGCCA AGCAGTGATG GATCTGGCTG CTGTTGAAGG TCTAGATGCT CACCGCAATG    2580

CTGTTAAGGT TCGTATGGAG AAACTGGGAC TTATTTAATT ATTTAGAGAT TTTAACTTAC    2640

ATTTAGATTC GATAGATCC                                                 2659
```

(2) INFORMATION FOR SEQ ID NO:20:

(i) SEQUENCE CHARACTERISTICS:
      (A) LENGTH: 844 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:20:

```
Met Thr Phe Pro Leu Leu Pro Ala Tyr Ala Ser Val Ala Glu Phe Asp
1               5                   10                  15

Asn Ser Leu Ser Leu Val Gly Lys Ala Val Phe Pro Tyr Ala Ala Asp
            20                  25                  30

Gln Leu His Asn Leu Ile Lys Phe Thr Gln Ser Thr Glu Leu Gln Val
        35                  40                  45

Asn Val Gln Val Glu Ser Ser Val Thr Glu Asp Gln Phe Glu Glu Leu
    50                  55                  60

Ile Asp Asn Leu Leu Lys Leu Tyr Asn Asn Gly Ile Asn Glu Val Ile
65                  70                  75                  80

Leu Asp Leu Asp Leu Ala Glu Arg Val Gln Arg Met Ile Pro Gly
                85                  90                  95

Ala Arg Val Ile Tyr Arg Thr Leu Val Asp Lys Val Ala Ser Leu Pro
            100                 105                 110

Ala Asn Ala Ser Ile Ala Val Pro Phe Ser Ser Pro Leu Gly Asp Leu
        115                 120                 125

Lys Ser Phe Thr Asn Gly Gly Ser Arg Thr Val Tyr Ala Phe Ser Glu
    130                 135                 140

Thr Ala Lys Leu Val Asp Val Ser Thr Val Ala Ser Gly Ile Ile
145                 150                 155                 160
```

```
Pro Ile Ile Asp Ala Arg Gln Leu Thr Thr Glu Tyr Glu Leu Ser Glu
                165                 170                 175
Asp Val Lys Lys Phe Pro Val Ser Glu Ile Leu Leu Ala Ser Leu Thr
            180                 185                 190
Thr Asp Arg Pro Asp Gly Leu Phe Thr Thr Leu Val Ala Asp Ser Ser
        195                 200                 205
Asn Tyr Ser Leu Gly Leu Val Tyr Ser Ser Lys Ser Ile Pro Glu
    210                 215                 220
Ala Ile Arg Thr Gln Thr Gly Val Tyr Gln Ser Arg His Gly Leu
225                 230                 235                 240
Trp Tyr Lys Gly Ala Thr Ser Gly Ala Thr Gln Lys Leu Leu Gly Ile
                245                 250                 255
Glu Leu Asp Cys Asp Gly Asp Cys Leu Lys Phe Val Val Glu Gln Thr
            260                 265                 270
Gly Val Gly Phe Cys His Leu Glu Arg Thr Ser Cys Phe Gly Gln Ser
        275                 280                 285
Lys Gly Leu Arg Ala Met Glu Ala Thr Leu Trp Asp Arg Lys Ser Asn
    290                 295                 300
Ala Pro Glu Gly Ser Tyr Thr Lys Arg Leu Phe Asp Asp Glu Val Leu
305                 310                 315                 320
Leu Asn Ala Lys Ile Arg Glu Glu Ala Asp Glu Leu Ala Glu Ala Lys
                325                 330                 335
Ser Lys Glu Asp Ile Ala Trp Glu Cys Ala Asp Leu Phe Tyr Phe Ala
            340                 345                 350
Leu Val Arg Cys Ala Lys Tyr Gly Val Thr Leu Asp Glu Val Glu Arg
        355                 360                 365
Asn Leu Asp Met Lys Ser Leu Lys Val Thr Arg Arg Lys Gly Asp Ala
    370                 375                 380
Lys Pro Gly Tyr Thr Lys Glu Gln Pro Lys Glu Glu Ser Lys Pro Lys
385                 390                 395                 400
Glu Val Pro Ser Glu Gly Arg Ile Glu Leu Cys Lys Ile Asp Val Ser
                405                 410                 415
Lys Ala Ser Ser Gln Glu Ile Glu Asp Ala Leu Arg Arg Pro Ile Gln
            420                 425                 430
Lys Thr Glu Gln Ile Met Glu Leu Val Lys Pro Ile Val Asp Asn Val
        435                 440                 445
Arg Gln Asn Gly Asp Lys Ala Leu Leu Glu Leu Thr Ala Lys Phe Asp
    450                 455                 460
Gly Val Ala Leu Lys Thr Pro Val Leu Glu Ala Pro Phe Pro Glu Glu
465                 470                 475                 480
Leu Met Gln Leu Pro Asp Asn Val Lys Arg Ala Ile Asp Leu Ser Ile
                485                 490                 495
Asp Asn Val Arg Lys Phe His Glu Ala Gln Leu Thr Glu Thr Leu Gln
            500                 505                 510
Val Glu Thr Cys Pro Gly Val Val Cys Ser Arg Phe Ala Arg Pro Ile
        515                 520                 525
Glu Lys Val Gly Leu Tyr Ile Pro Gly Gly Thr Ala Ile Leu Pro Ser
    530                 535                 540
Thr Ser Leu Met Leu Gly Val Pro Ala Lys Val Ala Gly Cys Lys Glu
545                 550                 555                 560
Ile Val Phe Ala Ser Pro Pro Lys Lys Asp Gly Thr Leu Thr Pro Glu
                565                 570                 575
Val Ile Tyr Val Ala His Lys Val Gly Ala Lys Cys Ile Val Leu Ala
```

-continued

```
              580                 585                 590
    Gly Gly Ala Gln Ala Val Ala Ala Met Ala Tyr Gly Thr Glu Thr Val
                595                 600                 605

Pro Lys Cys Asp Lys Ile Phe Gly Pro Gly Asn Gln Phe Val Thr Ala
        610                 615                 620

Ala Lys Met Met Val Gln Asn Asp Thr Ser Ala Leu Cys Ser Ile Asp
    625                 630                 635                 640

Met Pro Ala Gly Pro Ser Glu Val Leu Val Ile Ala Asp Lys Tyr Ala
                    645                 650                 655

Asp Pro Asp Phe Val Ala Ser Asp Leu Leu Ser Gln Ala Glu His Gly
                660                 665                 670

Ile Asp Ser Gln Val Ile Leu Leu Ala Val Asp Met Thr Asp Lys Glu
            675                 680                 685

Leu Ala Arg Ile Glu Asp Ala Val His Asn Gln Ala Val Gln Leu Pro
        690                 695                 700

Arg Val Glu Ile Val Arg Lys Cys Ile Ala His Ser Thr Thr Leu Ser
    705                 710                 715                 720

Val Ala Thr Tyr Glu Gln Ala Leu Glu Met Ser Asn Gln Tyr Ala Pro
                    725                 730                 735

Glu His Leu Ile Leu Gln Ile Glu Asn Ala Ser Ser Tyr Val Asp Gln
                740                 745                 750

Val Gln His Ala Gly Ser Val Phe Val Gly Ala Tyr Ser Pro Glu Ser
            755                 760                 765

Cys Gly Asp Tyr Ser Ser Gly Thr Asn His Thr Leu Pro Thr Tyr Gly
    770                 775                 780

Tyr Ala Arg Gln Tyr Ser Gly Val Asn Thr Ala Thr Phe Gln Lys Phe
    785                 790                 795                 800

Ile Thr Ser Gln Asp Val Thr Pro Glu Gly Leu Lys His Ile Gly Gln
                    805                 810                 815

Ala Val Met Asp Leu Ala Ala Val Glu Gly Leu Asp Ala His Arg Asn
                820                 825                 830

Ala Val Lys Val Arg Met Glu Lys Leu Gly Leu Ile
            835                 840
```

(2) INFORMATION FOR SEQ ID NO:21:

(i) SEQUENCE CHARACTERISTICS:
     (A) LENGTH: 48 amino acids
     (B) TYPE: amino acid
     (C) STRANDEDNESS: single
     (D) TOPOLOGY: linear (ii) MOLECULE TYPE: peptide (xi) SEQUENCE DESCRIPTION: SEQ ID NO:21:

```
    Met Leu Ile Ile Val Leu Leu Phe Leu Ala Thr Leu Ala Asn Ser Leu
    1               5                   10                  15

Asp Cys Ser Gly Asp Val Phe Phe Gly Tyr Thr Arg Gly Asp Lys Thr
                20                  25                  30

Asp Val His Lys Ser Gln Asn Leu Thr Ala Val Lys Asn Ile Lys Arg
            35                  40                  45
```

(2) INFORMATION FOR SEQ ID NO:22:

(i) SEQUENCE CHARACTERISTICS:
     (A) LENGTH: 48 amino acids
     (B) TYPE: amino acid
     (C) STRANDEDNESS: single (D) TOPOLOGY: linear (ii) MOLECULE TYPE: peptide (xi) SEQUENCE DESCRIPTION: SEQ ID NO:22:

Met Leu Ile Ile Val Leu Leu Phe Leu Ala Thr Leu Ala Asn Ser Leu
    1               5                   10                  15

Asp Cys Ser Gly Asp Val Phe Phe Gly Tyr Thr Arg Gly Asp Lys Thr
                20                  25                  30

Asp Val His Lys Ser Gln Asn Leu Thr Ala Val Pro Met Tyr Lys Arg
            35                  40                  45

(2) INFORMATION FOR SEQ ID NO:23:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Met Leu Ile Ile Val Leu Leu Phe Leu Ala Thr Leu Ala Asn Ser Leu
    1               5                   10                  15

Asp Cys Ser Gly Asp Val Phe Phe Gly Tyr Thr Arg Gly Asp Lys Thr
                20                  25                  30

Asp Val His Lys Ser Gln Ala Leu Thr Ala Val Pro Met Tyr Lys Arg
            35                  40                  45

(2) INFORMATION FOR SEQ ID NO:24:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:24:

AATTCGACAG AATGTTAATT ATAGTCTTAT TATTTTTAGC TACTTTAGCT AATTCCCTCG      60

ATTGTAGC                                                              68

(2) INFORMATION FOR SEQ ID NO:25:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:25:

GGAGATGTAT TTTTTGGATA TACTAGAGGA GACAAAACAG ATGTTCATAA AAGT            54

(2) INFORMATION FOR SEQ ID NO:26:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:26:

GGTCCAGAAA CCTTGTGTGG TGCTGAATTG GTCGATGCTT TGCAATTC                    48

(2) INFORMATION FOR SEQ ID NO:27:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:27:

GTTTGTGGTG ACAGAGGTTT CTACTTCAAC AAGCCAACCG GTTACGGTTC TTCTT           55

(2) INFORMATION FOR SEQ ID NO:28:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:28:

CTAGAAGAGC TCCACAAACC GGTATCGTTG ACGAATGTTG TTTCA                       45

(2) INFORMATION FOR SEQ ID NO:29:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:29:

AATTAGCTAA AGTACGTAAA AATAATAAGA CTATAATTAA CATTCTGTCG                  50

(2) INFORMATION FOR SEQ ID NO:30:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Synthetic"

(xi) SEQUENCE DESCRIPTION: SEQ ID NO:30:

ATCTGTTTTG TCTCCTCTAG TATATCCAAA AAATACATCT CCGCTACATT CGAGGG          56

(2) INFORMATION FOR SEQ ID NO:31:

(i) SEQUENCE CHARACTERISTICS:
            (A) LENGTH: 48 base pairs
            (B) TYPE: nucleic acid
            (C) STRANDEDNESS: single (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:31:

GTCACCACAA ACGAATTGCA AAGCATCGAC CAATTCAGCA CCACACAA                48

(2) INFORMATION FOR SEQ ID NO:32:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:32:

GGTTTCTGGA CCTCTTTTAA TATTTTTAAC CGCTGTTAAG TTTTGACTTT TATGAAC       57

(2) INFORMATION FOR SEQ ID NO:33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:33:

CAAGCATTAA CAGCGGTTCC AATGTACAAA AGA                                 33

(2) INFORMATION FOR SEQ ID NO:34:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:34:

GGTTTCTGGA CCTCTTTTGT ACATTGGAAC CGCTGTTAAT GCTTGACTTT TATGAAC       57

(2) INFORMATION FOR SEQ ID NO:35:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:35:

CAAAACTTAA CAGCGGTTCC AATGTACAAA AGA                                 33

(2) INFORMATION FOR SEQ ID NO:36:

(i) SEQUENCE CHARACTERISTICS:
        (A) LENGTH: 55 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:36:

GAGCTCTTCT AGAAGAAGAA CCGTAACCGG TTGGCTTGTT GAAGTAGAAA CCTCT            55

(2) INFORMATION FOR SEQ ID NO:37:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:37:

GATCTGAAAC AACATTCGTC AACGATACCG GTTTGTG                                37

(2) INFORMATION FOR SEQ ID NO:38:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:38:

AATTCTTATC AAGCAGACTT AGCTGGCTTC AATGGAGCAC AGTACATTTC CAATCTTCTC       60

AAGTCACAG                                                              69

(2) INFORMATION FOR SEQ ID NO:39:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:39:

CAAAACTTAA CAGCGGTTAA AAATATTAAA AGA                                    33

(2) INFORMATION FOR SEQ ID NO:40:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic"

(xi) SEQUENCE DESCRIPTION: SEQ ID NO:40:

GGTTTCTGGA CCTCTTTTGT ACATTGGAAC CGCTGTTAAG TTTTGACTTT TATGAAC          57
```

PICHIA SECRETORY LEADER FOR PROTEIN EXPRESSION

This application claims benefit of Provisional application Serial No. 60/004,264 filed Sep. 25, 1995, and a provision of Serial No. 60/004,327 filed Sep. 26, 1995.

BACKGROUND OF THE INVENTION

Recombinant DNA technology has revolutionized the ability to produce polypeptides economically. Yeast host cells and expression systems are useful for such production. Examples of yeast expression systems are Brake, U.S. Pat. No. 4,870,008; Cregg, U.S. Pat. No. 4,837,148; Stroman et al., U.S. Pat. No. 4,855,231; Stroman et al. U.S. Pat. No. 4,879,231; Brierley et al., U.S. Pat. No. 5,324,639; Prevatt et al., U.S. Pat. No. 5,330,901; Tschopp, EP 256 421; Sreekrishna et al., *J. Basic Microbiol.* 28(1988): 4 265–278; Tschopp et al., *Bio/Technology* 5(1987): 1305–1308; Cregg et al., *Bio/Technology* 5(1987): 479–485; Sreekrishna et al. *Biochemistry* 28(1989): 4117–4125; and Bolen et al., *Yeast* 10: 403–414 (1994).

General recombinant DNA methods can be found, for example, in Sambrook et al., *Molecular Cloning: A Laboratory Manual* (2nd ed., 1989).

All publications, patents and patent applications cited herein, whether supra or infra, are hereby incorporated by reference in their entirety.

SUMMARY OF THE INVENTION

It is an object of the invention to provide a polynucleotide molecule comprising a first nucleotide sequence that encodes at least a fragment of a leader sequence and a second nucleotide sequence that encodes a polypeptide heterologous to the leader sequence, wherein the leader sequence fragment is sufficient for secretion and comprises an amino acid sequence that comprises at least about 70% sequence identity to the leader sequence of *Pichia acaciae* killer toxin, wherein the heterologous polypeptide is not naturally contiguous to the leader sequence, and wherein upon expression of the polynucleotide molecule in a host cell suitable for expression thereof, the heterologous polypeptide is produced that is free of additional N-terminal amino acids.

The polynucleotide of the invention can be used to construct expression vectors and host cells capable of producing the polynucleotide or expressing the desired polypeptide.

Yet another object of the invention is to provide a method of producing a polypeptide encoded by a polynucleotide comprising (a) transforming a host cell with the polynucleotide, (b) allowing the expression thereof to produce the polypeptide and (c) obtaining the polypeptide therefrom, wherein the polynucleotide molecule comprises a first nucleotide sequence that encodes at least a fragment of a leader sequence and a second nucleotide sequence that encodes a polypeptide heterologous to the leader sequence, wherein the leader sequence fragment is sufficient for secretion and comprises an amino acid sequence that comprises at least about 70% sequence identity to the leader sequence of *Pichia acaciae* killer toxin, wherein the heterologous polypeptide is not naturally contiguous to the leader sequence, and wherein upon expression of the polynucleotide molecule in a host cell suitable for expression thereof, the heterologous polypeptide is produced that is free of additional N-terminal amino acids.

A specific embodiment of the invention is where the heterologous polypeptide is human insulin-like growth factor 1 (IGF-1).

DETAILED DESCRIPTION

Definitions

Figure 1:
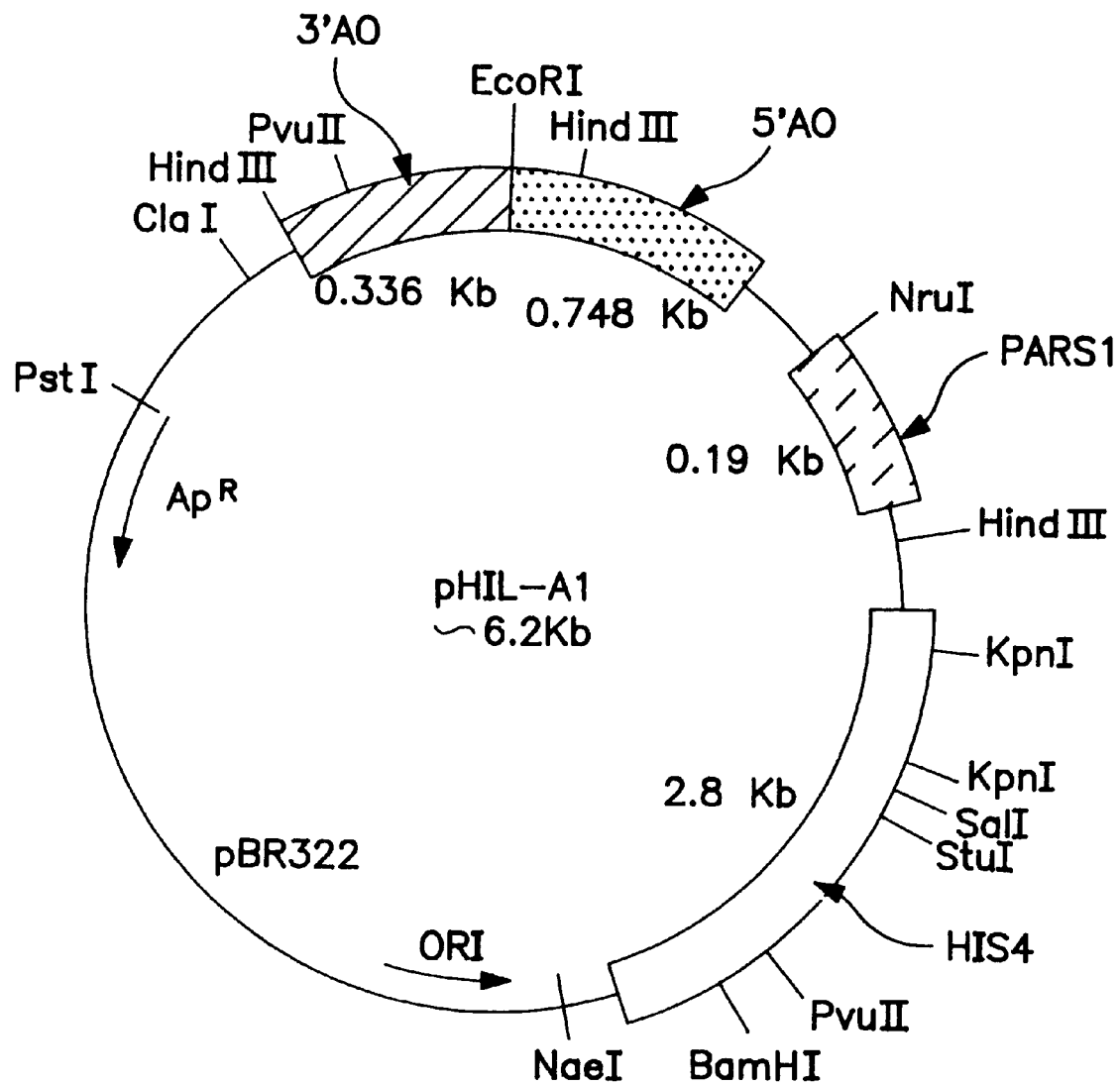
FIG. 1 is a plasmid map of pHIL-A1.

"Heterologous" means not naturally contiguous. For example, a yeast leader and a human protein are heterologous because the two are not naturally contiguous.

A host cell suitable of "expression of a polynucleotide" is capable of effecting transcription and translation of the polynucleotide to produce the encoded heterologous polypeptide free of additional N-terminal amino acids.

General Methods and Detailed Description

Preferably, polynucleotides of the instant invention are produced by recombinant DNA techniques. The polynucleotide encoding at least a fragment of a leader sequence can be either synthesized or cloned.

The amino acid sequence of the leader sequence comprises at least 70% sequence identity to the leader sequence of the *Pichia acaciae* killer toxin, described in Bolen et al., *Yeast* 10: 403–414 (1994) and shown in SEQ ID NO:2. More preferably, the leader sequence comprises at least 80%; even more preferably, at least 90%; more preferably, at least 95% sequence identity to SEQ ID NO:2; most preferably, 100% sequence identity to SEQ ID NO:2.

A full length leader sequence begins at the initiating methionine and ends at the last amino acid residue before the beginning of the encoded mature polypeptide. Amino acid residues can be removed from full length leader to construct leader fragments. These fragments can be tested to determine if they are sufficient for secretion.

Empirical data can be used, for example, to determine if a fragment of a leader sequence is sufficient for secretion. Host cells with the polynucleotide of the instant invention exhibit increased expression levels as compared to a negative control. See below for assays to detect polypeptide expression.

A full length leader sequence from a native gene, such a *Pichia acaciae* killer toxin, can be divided into a signal peptide region and a pro-region. Typically, a fragment sufficient for secretion comprises a signal peptide. Signal peptides are generally hydrophobic and exhibit a three dimensional helical structure. Also, a cleavage site can be incorporated in the fragment to facilitate removal of the leader fragment from the heterologous polypeptide. Examples are peptidase cleavage sites, which include KEX2 as an example. Preferably, the cleavage site comprises a dibasic dipeptide such as, lys—lys, arg—arg, more preferably lys-arg.

The leader sequence can be altered for convenience or to optimize expression. For example, the amino acid sequence of *Pichia acaciae* signal peptide can be mutated. The following are examples of conservative substitutions: Gly⇔Ala; Val⇔Ile⇔Leu; Asp⇔Glu; Lys⇔Arg; Asn⇔Gln; and Phe⇔Trp⇔Tyr. A subset of mutants, called muteins, is a group of polypeptides with the non-disulfide bond participating cysteines substituted with a neutral amino acid, generally, with serines.

The amino acid sequence of the *Pichia acaciae* killer toxin leader sequence, SEQ ID NO:2 can be aligned with the leader sequence of other yeast killer toxin genes to determine the positions of variable and conserved amino acid residues.

Full length and fragments of *Pichia acaciae* killer toxin leader sequences as well as mutants thereof, can be fused with additional amino acid residues. For example, the consensus sequence of pro-regions from other leader sequences can be determined and incorporated into the leader sequence. Such pro-region sequences can be helpful to optimize expression in a particular host cell.

Polynucleotide sequence encoding the leader sequence can be based on the sequence found in genomic DNA or be made by using codons preferred by the host cell. In both cases, the polynucleotides can be synthesized using the methods described in Urdea et al., *Proc. Natl. Acad. Sci. USA* 80: 7461 (1983), for example. Alternatively, the polynucleotides from nucleic acid libraries using probes based on the nucleic acid sequence shown in SEQ ID NO:1. Techniques for producing and probing nucleic acid sequence libraries are described, for example, in Sambrook et al., "Molecular Cloning: A Laboratory Manual" (New York, Cold Spring Harbor Laboratory, 1989). Other recombinant techniques, such as site specific mutagenesis, PCR, enzymatic digestion and ligation, can also be used to clone or modify the sequences found from natural sources.

Similarly, the polynucleotides encoding the desired polypeptide can also be constructed using synthetic or recombinant means. Amino acid sequence of polypeptides to be expressed can also be found in publically available databases.

Useful polypeptides to be expressed include, for example, hormones, growth factors, cytokines, haematopoietic factors, immunoglobulins, enzymes, repressors, cell differentiation factors, binding proteins, or transcription factors. Specific examples are: growth hormone, luteinizing hormone, thyroid stimulating hormone, oxytocin, insulin, vasopressin, renin, calcitonin, follicle stimulating hormone, prolactin, insulin-like growth factor (IGF-I, IGF-II), an IGF-binding protein, epidermal growth factor (EGF), platelet derived growth factor (PDGF), keratinocyte growth factor (KGF), fibroblast growth factor (FGF), nerve growth factor (NGF), TGF-beta, vascular endothelial cell growth factor (VEGF), erythropoietin (EPO), colony stimulating factor (CSF), interferon, endorphin, enkaphalin, dynorphin and an active fragment thereof.

The two polynucleotides, encoding at least a fragment of a leader sequence and the heterologous polypeptide, are linked together to produce the polynucleotide of the instant invention. Preferably, the polynucleotides are linked together in proper reading frame.

Polynucleotides encoding at least a fragment of a leader sequence and encoding polypeptides can be expressed by a variety of host cells. Although the leader sequence may be yeast derived and linked to a human protein, for example, host cells as diverse as yeast, insect, and mammalian host cells can express the polypeptide.

Typically, the polynucleotide of the instant invention, leader sequence and polypeptide, can be incorporated into an expression vector, which is in turn inserted into the desired host cell for expression.

At the minimum, an expression vector will contain a promoter which is operable in the host cell and operably linked to polynucleotide of the instant invention. Expression vectors may also include signal sequences, terminators, selectable markers, origins of replication, and sequences homologous to host cell sequences. These additional elements are optional but can be included to optimize expression.

A promoter is a DNA sequence upstream or 5' to the polynucleotide of the instant invention to be expressed. The promoter will initiate and regulate expression of the coding sequence in the desired host cell. To initiate expression, promoter sequences bind RNA polymerase and initiate the downstream (3') transcription of a coding sequence (e.g. structural gene) into mRNA. A promoter may also have DNA sequences that regulate the rate of expression by enhancing or specifically inducing or repressing transcription. These sequences can overlap the sequences that initiate expression. Most host cell systems include regulatory sequences within the promoter sequences. For example, when a repressor protein binds to the lac operon, an *E. coli* regulatory promoter sequence, transcription of the downstream gene is inhibited. Another example is the yeast alcohol dehydrogenase promoter, which has an upstream activator sequence (UAS) that modulates expression in the absence of glucose. Additionally, some viral enhancers not only amplify but also regulate expression in mammalian cells. These enhancers can be incorporated into mammalian promoter sequences, and the promoter will become active only in the presence of an inducer, such as a hormone or enzyme substrate (Sassone-Corsi and Borelli (1986) *Trends Genet.* 2:215; Maniatis et al. (1987) *Science* 236:1237).

Functional non-natural promoters may also be used, for example, synthetic promoters based on a consensus sequence of different promoters. Also, effective promoters can contain a regulatory region linked with a heterologous expression initiation region. Examples of hybrid promoters are the *E. coli* lac operator linked to the *E. coli* tac transcription activation region; the yeast alcohol dehydrogenase (ADH) regulatory sequence linked to the yeast glyceraldehyde-3-phosphate-dehydrogenase (GAPDH) transcription activation region (U.S. Pat. Nos. 4,876,197 and 4,880,734, incorporated herein by reference); and the cytomegalovirus (CMV) enhancer linked to the SV40 (simian virus) promoter.

Typically, terminators are regulatory sequences, such as polyadenylation and transcription termination sequences, located 3' or downstream of the stop codon of the coding sequences. Usually, the terminator of native host cell proteins are operable when attached 3' of the polynucleotide of the instant invention. Examples are the *Saccharomyces cerevisiae* alpha-factor terminator and the baculovirus terminator. Further, viral terminators are also operable in certain host cells; for instance, the SV40 terminator is functional in CHO cells.

For convenience, selectable markers, an origin of replication, and homologous host cell sequences may optionally be included in an expression vector. A selectable marker can be used to screen for host cells that potentially contain the expression vector. Such markers may render the host cell immune to drugs such as ampicillin, chloramphenicol, erythromycin, neomycin, and tetracycline. Also, markers may be biosynthetic genes, such as those in the histidine, tryptophan, and leucine biosynthetic pathways. Thus, when leucine is absent from the media, for example, only the cells with a biosynthetic gene in the leucine pathway will survive.

An origin of replication may be needed for the expression vector to replicate in the host cell. Certain origins of replication enable an expression vector to be reproduced at a high copy number in the presence of the appropriate proteins within the cell. Examples of origins are the 2m and autonomously replicating sequences, which are effective in yeast; and the viral T-antigen, effective in COS-7 cells.

Expression vectors may be integrated into the host cell genome or remain autonomous within the cell. Polynucleotide sequences homologous to sequences within the host cell genome may be needed to integrate the expression cassette. The homologous sequences do not always need to be linked to the expression vector to be effective. For example, expression vectors can integrate into the CHO genome via an unattached dihydrofolate reductase gene. In yeast, it is more advantageous if the homologous sequences flank the expression cassette. Particularly useful homologous yeast genome sequences are those disclosed in PCT WO90/01800, and the HIS4 gene sequences, described in Genbank, accession no. J01331.

The choice of promoter, terminator, and other optional elements of an expression vector will also depend on the host cell chosen. The invention is not dependent on the host cell selected. Convenience and the level of protein expression will dictate the optimal host cell. A variety of hosts for expression are known in the art and available from the American Type Culture Collection (ATCC). Bacterial hosts suitable for expression include, without limitation: Campylobacter, Bacillus, Escherichia, Lactobacillus, Pseudomonas, Staphylococcus, and Streptococcus. Yeast hosts from the following genera may be utilized: Candida, Hansenula, Kluyveromyces, Pichia, Saccharomyces, Schizosaccharomyces, and Yarrowia. Immortalized mammalian host cells include but are not limited to CHO cells, HeLa cells, baby hamster kidney (BHK) cells, monkey kidney cells (COS), human hepatocellular carcinoma cells (e.g. Hep G2), and other cell lines. A number of insect cell hosts are also available for expression of heterologous proteins: *Aedes aegypti*, *Bombyx mori*, *Drosophila melanogaster*, and *Spodoptera frugiperda* (PCT WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Transformation

After vector construction, the expression vector is inserted into the host cell. Many transformation techniques exist for inserting expression vectors into bacterial, yeast, insect, and mammalian cells. The transformation procedure to introduce the expression vector depends upon the host to be transformed.

Methods of introducing exogenous DNA into bacterial hosts are well-known in the art, and typically protocol includes either treating the bacteria with $CaCl_2$ or other agents, such as divalent cations and DMSO. DNA can also be introduced into bacterial cells by electroporation or viral infection. Transformation procedures usually vary with the bacterial species to be transformed. See e.g., (Masson et al. (1989) *FEMS Microbiol. Lett.* 60:273; Palva et al. (1982) *Proc. Natl. Acad. Sci. USA* 79:5582; EP Publ. Nos. 036 259 and 063 953; PCT WO 84/04541, Bacillus), (Miller et al. (1988) *Proc. Natl. Acad. Sci.* 85:856; Wang et al. (1990) *J. Bacteriol.* 172:949, Campylobacter), (Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids," in *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; Escherichia), (Chassy et al. (1987) *FEMS Microbiol. Lett.* 44:173 Lactobacillus); (Fiedler et al. (1988) *Anal. Biochem* 170:38, Pseudomonas); (Augustin et al. (1990) *FEMS Microbiol. Lett.* 66:203, Staphylococcus), (Barany et al. (1980) *J. Bacteriol.* 144:698; Harlander (1987) "Transformation of *Streptococcus lactis* by electroporation," in *Streptococcal Genetics* (ed. J. Ferretti and R. Curtiss III); Perry et al. (1981) *Infec. Immun.* 32:1295; Powell et al. (1988) *Appl. Environ. Microbiol.* 54:655, Somkuti et al. (1987) *Proc. 4th Evr. Cong. Biotechnology* 1:412, Streptococcus).

Transformation methods for yeast hosts are well-known in the art, and typically include either the transformation of spheroplasts or of intact yeast cells treated with alkali cations. Electroporation is another means for transforming yeast hosts. See for example, *Methods in Enzymology*, Volume 194, 1991, "Guide to Yeast Genetics and Molecular Biology." Transformation procedures usually vary with the yeast species to be transformed. See e.g., (Kurtz et al. (1986) *Mol. Cell. Biol.* 6:142; Kunze et al. (1985) *J. Basic Microbiol.* 25:141; Candida); (Gleeson et al. (1986) *J. Gen. Microbiol.* 132:3459; Roggenkamp et al. (1986) *Mol. Gen. Genet.* 202:302; Hansenula); (Das et al. (1984) *J. Bacteriol.* 158:1165; De Louvencourt et al. (1983) *J. Bacteriol.* 154:1165; Van den Berg et al. (1990) *Bio/Technology* 8:135; Kluyveromyces); (Cregg et al. (1985) *Mol. Cell. Biol.* 5:3376; Kunze et al. (1985) *J. Basic Microbiol.* 25:141; U.S. Pat. Nos. 4,837,148 and 4,929,555: Pichia); (Hinnen et al. (1978) *Proc. Natl. Acad. Sci. USA* 75;1929; Ito et al. (1983) *J. Bacteriol.* 153:163 Saccharomyces); (Beach and Nurse (1981) *Nature* 300:706; Schizosaccharomyces); (Davidow et al. (1985) *Curr. Genet.* 10:39; Gaillardin et al. (1985) *Curr. Genet.* 10:49; Yarrowia).

Methods for introducing heterologous polynucleotides into mammalian cells are known in the art and include viral infection, dextran-mediated transfection, calcium phosphate precipitation, polybrene mediated transfection, protoplast fusion, electroporation, encapsulation of the polynucleotide (s) in liposomes, and direct microinjection of the DNA into nuclei.

The method for construction of an expression vector for transformation of insect cells for expression of recombinant protein herein is slightly different than that generally applicable to the construction of a bacterial expression vector, a yeast expression vector, or a mammalian expression vector. In an embodiment of the present invention, a baculovirus vector is constructed in accordance with techniques that are known in the art, for example, as described in Kitts et al., *BioTechniques* 14: 810–817 (1993), Smith et al., *Mol. Cell. Biol.* 3: 2156 (1983), and Luckow and Summer, *Virol.* 17: 31(1989). In one embodiment of the present invention, a baculovirus expression vector is constructed substantially in accordance to Summers and Smith, Texas Agricultural Experiment Station Bulletin No. 1555 (1987). Moreover, materials and methods for baculovirus/insect cell expression systems are commercially available in kit form, for example, the MaxBac® kit from Invitrogen (San Diego, Calif.).

Also, methods for introducing heterologous DNA into an insect host cell are known in the art. For example, an insect cell can be infected with a virus containing a coding sequence. When the virus is replicating in the infected cell, the polypeptide will be expressed if operably linked to a suitable promoter. A variety of suitable insect cells and viruses are known and include following without limitation.

Insect cells from any order of the Class Insecta can be grown in the media of this invention. The orders Diptera and Lepidoptera are preferred. Example of insect species are listed in Weiss et al., "Cell Culture Methods for Large-Scale Propagation of Baculoviruses.," in Granados et al. (eds.), *The Biology of Baculoviruses: Vol. II Practical Application for Insect Control*, pp. 63–87 at p. 64 (1987). Insect cell lines derived from the following insects are exemplary: *Carpocapsa pomeonella* (preferably, cell line CP-128); *Trichoplusia ni* (preferably, cell line TN-368); *Autograph californica; Spodoptera frugiperda* (preferably, cell line Sf9); *Lymantria dispar; Mamestra brassicae; Aedes albopictus; Orgyia pseudotsugata; Neodiprio sertifer; Aedes aegypti; Antheraea eucalypti; Gnorimoschema operceullela; Galleria mellonella; Spodoptera littolaris; Blatella germanic; Drosophila melanogaster; Heliothis zea; Spodoptera exigua; Rachiplusia ou; Plodia interpunctella; Amsaeta moorei; Agrotis c-nigrum, Adoxophyes orana; Agrotis segetum; Bombyx mori; Hyponomeuta malinellu;, Colias eurytheme; Anticarsia germmetalia; Apanteles melanoscelu; Arctia caja;* and *Porthetria dispar.* Preferred insect cell lines are from *Spodoptera frugiperda*, and especially preferred is cell line Sf9. The Sf9 cell line used in the examples herein was obtained from Max D. Summers (Texas A & M University, College Station, Tex., 77843, U.S.A.) Other *S. frugiperda* cell lines, such as IPL-Sf-21AE III, are described in Vaughn et al., *In Vitro* 13: 213–217 (1977).

The insect cell lines of this invention are suitable for the reproduction of numerous insect-pathogenic viruses such as parvoviruses, pox viruses, baculoviruses and rhabdcoviruses, of which nucleopolyhedrosis viruses (NPV) and granulosis viruses (GV) from the group of baculoviruses are preferred. Further preferred are NPV viruses such as those from Autographa spp., Spodoptera spp., Trichoplusia spp., Rachiplusia spp., Gallerai spp., and Lymantria spp. More preferred are baculovirus strain *Autographa californica* NPV (AcNPV), *Rachiplusia ou* NPV, *Galleria mellonella* NPV, and any plaque purified strains of AcNPV, such as E2, R9, S1, M3, characterized and described by Smith et al., *J Virol* 30: 828–838 (1979); Smith et al., *J Virol* 33: 311–319 (1980); and Smith et al., *Virol* 89: 517–527 (1978).

Typically, insect cells *Spodoptera frugiperda* type 9 (SF9) are infected with baculovirus strain *Autographa californica* NPV (AcNPV) containing a coding sequence. Such a baculovirus is produced by homologous recombination between a transfer vector containing the coding sequence and baculovirus sequences and a genomic baculovirus DNA. Preferably, the genomic baculovirus DNA is linearized and contains a disfunctional essential gene. The transfer vector, preferably, contains the nucleotide sequences needed to restore the disfunctional gene and a baculovirus polyhedrin promoter and terminator operably linked to the polynucleotides of the instant invention. (See Kitts et al., *BioTechniques* 14(5): 810–817 (1993).

The transfer vector and linearized baculovirus genome are transfected into SF9 insect cells, and the resulting viruses probably containing the desired coding sequence. Without a functional essential gene the baculovirus genome cannot produce a viable virus. Thus, the viable viruses from the transfection most likely contain the coding sequence and the needed essential gene sequences from the transfer vector. Further, lack of occlusion bodies in the infected cells are another verification that the coding sequence was incorporated into the baculovirus genome.

The essential gene and the polyhedrin gene flank each other in the baculovirus genome. The coding sequence in the transfer vector is flanked at its 5' with the essential gene sequences and the polyhedrin promoter and at its 3' with the polyhedrin terminator. Thus, when the desired recombination event occurs the coding sequence displaces the baculovirus polyhedrin gene. Such baculoviruses without a polyhedrin gene will not produce occlusion bodies in the infected cells. Of course, another means for determining if coding sequence was incorporated into the baculovirus genome is to sequence the recombinant baculovirus genomic DNA. Alternatively, expression of the desired polypeptide by cells infected with the recombinant baculovirus is another verification means.

Once transformed the host cells can be used to produce either polynucleotides of the instant invention or express the desired polypeptide.

Simple gel electrophoresis techniques can be used to detect expression of the desired polypeptide. For example, media from a host cell without an expression vector can be compared to media from host cell with the desired vector. Polyacrylamide gel electrophoresis ("PAGE") can be used to determine if any proteins were expressed. Antibodies to the desired proteins can be used in Western blots to determine with greater sensitivity if protein was expressed.

EXAMPLES

The examples presented below are provided as a further guide to the practitioner of ordinary skill in the art, and are not to be construed as limiting the invention in any way.

Example 1

Construction of *Pichia pastoris* autonomously replicating vector containing *P. pastoris* HIS4 gene (SEQ ID NO:19) as a selectable marker and an expression cassette (SEQ ID NO:13) containing a *P. acaciae* killer toxin leader and IGF-1 gene.

A. CLONING

I. Killer Toxin Leader Fragment

Construction of fragment by annealing of synthetic oligomers.

Synthesis of oligomers with a phosphate group attached or kinase.

The sequence of the oligomers, KAC 34, KAC 37, KAC 39, KAC 59, KAC 60, and KAC 61 are set forth in SEQ ID NOs:3, 4, 5, 6, 7, and 8, respectively.

Ligation of fragment and base vector for sequencing and ease of handling

Fragment: as described above

Base vector: pLITMUS28 available from New England Biolabs (Beverly, Mass., USA)

II. IGF-1 Fragment

Isolation: from a yeast strain with an integrated vector. Sequence of gene attached.

III. Overlapping PCR

Construction of a single fragment containing the leader sequence and IGF-1 gene.

PCR #1

Reaction Mix

4 $\mu$L of IGF-1 gene fragment for a total of 10 ng

10 $\mu$L of Pfu DNA Polymerase buffer available from Stratagene (La Jolla, Calif., USA)

4 $\mu$L of a 2 mM dNTP

20 $\mu$L of oligomer KAC58 (SEQ ID NO:12) for a total of 20 picomoles

20 $\mu$L of oligomer KAC57 (SEQ ID NO:11) for a total of 20 picomoles

1 $\mu$L of 2.5 units/$\mu$L Pfu DNA Polymerase available from Stratagene (La Jolla, Calif., USA)

41 $\mu$L of water

Temperature cycle
5 cycles: 9° C. for 1 minute, 43° C. for 1 minute, and 72° C. for 1 minute
24 cycles: 97° C. for 1 minute and 72° C. for 1 minute
PCR#2
Reaction Mix
1 μL of Killer toxin fragment in pLITMUS28 for a total of 10 ng
10 μL of 10X PCR buffer
2 μL of 2 mM dNTP
10 μL of oligomer KAC74 (SEQ ID NO:9) for a total of 10 picomoles
10 μL of oligomer KAC75 (SEQ ID NO:10) for a total of 10 picomoles
0.5 μL of 5 units/μL taq DNA Polymerase available from Boehringer Mannheim catalog number 1 145 173 (Indianapolis, Ind., USA)
66.5 μL of $H_2O$
10X PCR buffer
0.25 M Tris-HCl, pH 8.3
0.015 M $MgCl_2$ in 0.0015 M EDTA
0.25 M KCl
0.5% Tween 20
Temperature cycle
5 cycles: 97° C. for 1 minute, 63° C. for 1 minute, and 72° C. for 1 minute
19 cycles: 97° C. for 1 minute and 72° C. for 1 minute
PCR #3
Reaction Mix
5 μL of result PCR#2
5 μL of 1:100 dilution of result of PCR#1
10 μL of 10X Pfu DNA Polymerase buffer available from Stratagene (La Jolla, Calif., USA)
4 μL of 2 mM dNTP
1 μL of 2.5 units/μL of Pfu DNA Polymerase available from Stratagene (La Jolla, Calif.)
2 μL of oligomer KAC74 (SEQ ID NO:9) for a total of 2 picomoles
2 μL of oligomer KAC57 (SEQ ID NO:11) for a total of 2 picomoles
71 μL of water.
Temperature Cycle
5 cycles: 97° C. for 1 minute, 58° C. for 1 minute, and 72° C. for 1 minute
24 cycles: 97° C. for 1 minute and 72° C. for 1 minute.
PCR#4
Reaction Mix
1 μL of results of PCR#3
10 μL of KAC74 (SEQ ID NO:9) for a total of 10 picomoles
30 μL of KAC57 (SEQ ID NO:11) for a total of 10 picomoles
10 μL of 10X PCR buffer (same as used in PCR#2)
2 μL of 2 mM dNTP
5 μL of 0.5 units/μL of taq DNA Polymerase available from Boehringer Mannheim catalog number 1 146 173 (Indianapolis, Ind., USA)
42 μL of water.

Temperature Cycle
24 cycles: 57° C. for 1 minute and 72° C. for 1 minute
Ligation of PCR#4 fragment to a shuttle vector for sequencing
Fragment: 1 μL of result of PCR#4
Base vector: 2 μL of pCRII from Invitrogen (San Diego, Calif., USA)
Ligase: 1 μL from Invitrogen (San Diego, Calif., USA) kit #45-0046
10X Ligase buffer: 1 μL from Invitrogen (San Diego, Calif., USA) kit #45-0046
Water: 5 μL
Ligation into Expression
Base Vector: 2 μL of pHIL-A1, linear with EcoRI ends and dephosphorylated
Fragment: 2 μL of EcoRI from pCRII with expression cassette containing a killer toxin leader fragment with IGF-1 gene
Ligase: 1 μL of T4 DNA ligase available from Boerhinger Mannheim
10X Ligase buffer: 1 μL available from Boerhinger Mannheim
Water: 4 μL
Verification that expression cassette in correct orientation by restriction endonuclease mapping. The nucleotide sequence for this expression cassette is set forth in SEQ ID NO:13, and the amino acid sequence for the encoded killer toxin leader fragment with IGF-I gene fragment is set forth in SEQ ID NO:14. SEQ ID NO:15 sets forth the C-terminal peptide fragment encoded by nucleotides 376–390 of the expression cassette set forth in SEQ ID NO:13.

Description of pHIL-A1

Plasmid pHIL-A1 is an E. coli-P. pastoris shuttle vector, with sequences for selection and autonomous replication in each host. One component of the plasmid is a modified portion of plasmid pBR322 containing the ampicillin resistance gene and the origin of replication (ori). The regions between nucleotides 1,100 and 2,485 of pBR322 and between NaeI sites 404 and 932 were deleted to eliminate "poison sequences" and the Sal I site, respectively.

The DNA elements comprising the rest of the plasmid are derived from the genome of P. pastoris, except for short regions of pBR322 used to the link the yeast elements. The yeast elements are as follows: proceeding clockwise:

1. 3' AOX1, alcohol oxidase, approximately 300 bp segment of the AO terminating sequence. See SEQ ID NO:16.
2. 5' AOX1, approximately 750 bp segment of the alcohol oxidase promoter. The alcohol oxidase coding sequences following the A of the ATG initiating methionine codon have been removed, and a synthetic linker used to generate a unique EcoRI site, as described for pHIL-D1 (available from Invitrogen, San Diego, Calif. USA). See SEQ ID NO:18.
3. PARS1, approximately 190 bp segment of P. pastoris autonomous replication sequence. See SEQ ID NO:17.
4. HIS4, approximately 2.8 kb segment of P. pastoris histidinol dehydrogenase gene to complement the defective his4 gene in P. pastoris, strain GS115. See SEQ ID NO:19.

Nucleotide sequence of the 3'AOX1 transcriptional termination region
(SEQ ID NO:16)

Eco RI
GAA TTC CCC TTA GAC ATG ACT GTT CCT CAG TTC AAG TTG GGC ACT TAC GAG AAG

ACC GGT CTT GCT AGA TTC TAA TCA AGA GGA TGT CAG AAT GCC ATT TGC CTG AGA

GAT GCA GGC TTC ATT TTT GAT ACT TTT TTA TTT GTA ACC TAT ATA GTA TAG GAT

3' end of AOX1 mRNA
TTT TTT TGT CAT TTT GTT TCT TCT CGT ACG AGC TTG CTC CTG ATC AGC CTA TCT

CGC AGC TGA TGA ATA TCT TGT GGT AGG GGT TTG GGA AAA TCA TTC GAG TTT GAT

GTT TTT CTT GGT ATT TCC CAC TCC TCT TCA GAG TAC AGA AGA TTA AGT GAG ACG

TTC GTT TGT GCA AGC TT
     Hind III
NOTE: The 3'AOX1 contains a small stretch (22 amino acids long) of carboxy terminal alcohol oxidase coding sequences upto translational stop codon TAA (italicized and underlined). The 3' end of AOX1 mRNA is in bold and also underlined (A).

Nucleotide Sequence of the PARS1 (154 bp) Taq I fragment in pHIL-A1
(SEQ ID NO:17)

Nru 1
TCG AGA TAA GCT GGG GGA ACA TTC GCG AAA ATG AAA CAA GTC GGC TGT TAT

Bgl II
AGT ATA TTT ATT ATA ATA TTG AAA GAT CTC AAA AGA CTA CTT ATT TTT GAA

Hinc II
TGA ACC AAG TAT GAA ATC AAC CTA TTT GGG GTT GAC CAA AAT AAG TAA ATA

TTA ATT GTC GA

Nucleotide sequence of 5'AOX1 (1018 Nucleotides)
SEQ ID NO:18

[5'AOX1 begins at (Hind III/Hinc II) in pHIL-Ds and pHIL-S1]
(Hind III/Hinc II) junction AAG CTG ACT CAT GTT GGT ATT GTG AAA TAG ACG CAG ATC GGG AAC ACT GAA AAA
         Bgl II
TAA CAG TTA TTA TTC GAG ATC TAA CAT CCA AAG ACG AAA GGT TGA ATG AAA CCT

TTT TGC CAT CCG ACA TCC ACA GGT CCA TTC TCA CAC ATA AGT GCC AAA CGC AAC

AGG AGG GGA TAC ACT AGC AGC AGA CCG TTG CAA ACG CAG GAC CTC CAC TCC TCT

TCT CCT CAA CAC CCA CTT TTG CCA TCG AAA AAC CAG CCC AGT TAT TGG GCT TGA
(5' AOXI of pHIL-A1 begins from Sst I)
 SstI
TTG GAG CTC GCT CAT TCC AAT TCC TTC TAT TAG GCT ACT AAC ACC ATG ACT TTA

TTA GCC TGT CTA TCC TGG CCC CCC TGG CGA GGT TCA TGT TTG TTT ATT TCC GAA

TGC AAC AAG CTC CGC ATT ACA CCC GAA CAT CAC TCC AGA TGA GGG CTT TCT GAG

TGT GGG GTC AAA TAG TTT CAT GTT CCC AAA ATG GCC AAA ACT GAC AGT TTA AAC

CGT GTC TTG GAA CCT AAT ATG ACA AAA GCG TGA TCT CAT CCA AGA TGA ACT AAG

GTT TGG TTC GTT GAA ATG CTA ACG GCC AGT TGG TCA AAA AGA AAC TTC CAA AAG

TCG GCA TAC CGT TTG TCT TGT TTG GTA TTG ATT GAC GAA TGC TCA AAA ATA ATC

TCA TTA ATG CTT AGC GCA GTC TCT CTA TCG CTT CTG AAC CCC GGT GCA CCT GTG

CCG AAA CGC AAA TGG GGA AAC ACC CGC TTT TTG GAT GAT TAT GCA TTG TCT CCA

CAT TGT ATG CTT CCA AGA TTC TGG TGG GAA TAC TGC TGA TAG CCT AAC GTT CAT

-continued
Nucleotide sequence of 5'AOX1 (1018 Nucleotides)
SEQ ID NO:18

```
GAT CAA AAT TTA ACT GTT CTA ACC CCT ACT TGA CAG CAA TAT ATA AAC AGA AGG
                                      ^       *
AAG CTG CCC TGT CTT AAA CCT TTT TTT TTA TCA TCA TTA TTA GCT TAC TTT CAT

AAT TGC GAC TGG TTC CAA TTG ACA AGC TTT TGA TTT TAA CGA CTT TTA ACG ACA
                                           AsuII/FspII      EcoRI
ACT TGA GAA GAT CAA AAA ACA ACT AAT TAT TCG AAA CGA GGA ATT C
```
Note: Nucleotides added immediately following the "A" of the translation initiation codon to create Eco RI site is italicized. The 5' end of the alcohol oxidase mRNA have been denoted as a major species (*) or minor species (^) of mRNA transcripts.

B. TRANSFORMATION
 I. Yeast Strain
 P. pastoris, GS115 available from Invitrogen (San Diego, Calif., USA), also available from the USDA, Northern Regional Research Center in Peoria, Ill., under the accession number NRRL Y-15851
or
 P. pastoris SMD1163
 II. Electroporation
 Cells: Cells from preculture at approximately 16 $OD_{600}$ 1:20 dilution into 10% glycerol with water. 50 µL of cells in 10% glycerol with water for electroporation.
 Equipment
 BioLab Pulse Controller and BioLab Gene Pulser
 Pulse
 2.0 Kilovolts
 25 µFD
 200 ohms
 Time Constant
 5 Milliseconds
 Selection
 Cells on minimal medium in minus histidine with glucose
C. EXPRESSION
 I. Precultures
 Media
 Minimal his minus media plus glucose
 Inoculum
 One transformed colony
 Temperature
 30° C.
 Time: until culture is saturated
 II. Expression Cultures
 Media: 25 mL of MGY
 MGY=
 13. g/L of Yeast Nitrogen Base without amino acids, available from Difco (Detroit, Mich., USA)
 400 µg/L biotin
 1% (v/v) glycerol
 0.1% leucine
 0.1% lysine
 0.1% tryptophan
 0.1% adenine
 0.1% uracil
 Inoculum
 250 µL of the preculture
 Temperature
 30° C.
 Aeration
 275 rpm
 Time
 Approximately 48 hours or 5–10 $OD_{600}$
 Harvest
 4000 rpm for 10 minutes
 Wash, Resuspension, and Dilution of cells
 Use MM media for all.
 MM=
 13. g/L of Yeast Nitrogen Base without amino acids, available from Difco (Detroit, Mich., USA)
 400 µg/L biotin
 0.5% (v/v) methanol
 0.1% leucine
 0.1% lysine
 0.1% tryptophan
 0.1% adenine
 0.1% uracil
 Resuspension: with approximately 5 mL
 Dilution: to approximately 3 $OD_{600}$.
 Temperature
 30° C.
 Aeration
 275 rpm
 Time
 Approximately 96 hours Example 2

Construction of Pichia pastoris integrating vector containing P. pastoris HIS4 gene (SEQ ID NO:19) as a selectable marker and multiple copies of an expression cassette (SEQ ID NO:13) containing the P. acaciae leader and IGF1 gene.
STAGE 1 CLONING
 Starting vector
 pAO815 as described by Brierley et al., U.S. Pat. No. 5,324,639 and available from Invitrogen (San Diego, Calif., USA). The vector contains a unique EcoRI restriction site flanked by the P. pastoris alcohol oxidase 1 ("AO1") gene promoter and terminator.
 Insert Fragment
 Described above in Example 1 comprising EcoRI restriction ends.
 Resulting vector 1
 One AO1 gene promoter
 One P. acaciae killer toxin leader
 One IGF-1 gene
 One AO1 gene terminator.
STAGE 2 CLONING
 Fragment
 BglII-BamHI fragment from Resulting vector 1.
 Base vector
 The entire resulting vector 1, linear with BamHI ends Resulting vector 2
pALIGF1–2 with two expression cassettes each with
  One AO1 gene promoter
  One P. acaciae killer toxin leader
  One IGF-1 gene
  One AO1 gene terminator.
STAGE 3
  Fragment
    BglII-BamHI fragment from Resulting vector 2, pALIGF1–2.
  Base Vector
    The entire pALIGF1–2, linear with BamHI ends
  Resulting Vector
    pALIGF1–3 with four expression cassettes with
      One AO1 gene promoter
      One P. acaciae killer toxin leader
      One IGF-1 gene
      One AO1 gene terminator.
STAGE 4
  Fragment
    BglII-BamHI fragment from Resulting vector 2, pALIGF1–2.
  Base Vector
    The entire pALIGF1–3, linear with BamHI ends
  Resulting Vector
    pALIGF1–4 with six expression cassettes with
      One AO1 gene promoter
      One P. acaciae killer toxin leader
      One IGF-1 gene
      One AO1 gene terminator.
TRANSFORMATION
  Yeast
    P. pastoris, GS115, available from Invitrogen (San Diego, Calif., USA) or P. pastoris, SMD1163.
  Electroporation: Same as Example 1.
  EXPRESSION: Same as Example 1.

Example 3

Construction of three vectors, pKK, pKG, and pKGK.

These vectors comprise the IGF-1 coding sequence. Further, the vectors comprise killer toxin leader sequences as described below:

(The asterisks indicate the amino acid positions that are different from the native killer toxin sequence.)

pKG=killer toxin leader with glycosylation site, sequence below:
Met-Leu-Ile-Ile-Val-Leu-leu-Phe-Leu-Ala-Thr-Leu-Ala-Asn-Ser-Leu-Asp-Cys-Ser-Gly-Asp-Val-Phe-Phe-Gly-Tyr-Thr-Arg-Gly-Asp-Lys-Thr-Asp-Val-His-Lys-Ser-Gln-Asn*-Leu-Thr-Ala-Val-Lys-Asn-Ile-Lys-Arg- (SEQ ID NO:21)

pKK=killer toxin with KEX2 site, sequence below:
Met-Leu-Ile-Ile-Val-Leu-leu-Phe-Leu-Ala-Thr-Leu-Ala-Asn-Ser-Leu-Asp-Cys-Ser-Gly-Asp-Val-Phe-Phe-Gly-Tyr-Thr-Arg-Gly-Asp-Lys-Thr-Asp-Val-His-Lys-Ser-Gln-Ala-Leu-Thr-Ala-Val-Pro*-Met*-Tyr*-Lys-Arg (SEQ ID NO:23)

pKGK=killer toxin with glycosylation site and KEX2 site, sequence below:
Met-Leu-Ile-Ile-Val-Leu-leu-Phe-Leu-Ala-Thr-Leu-Ala-Asn-Ser-Leu-Asp-Cys-Ser-Gly-Asp-Val-Phe-Phe-Gly-Tyr-Thr-Arg-Gly-Asp-Lys-Thr-Asp-Val-His-Lys-Ser-Gln-Asn*-Leu-Thr-Ala-Val-Pro*-Met*-Tyr*-Lys-Arg (SEQ ID NO:22)

A. ANNEALING OLIGOMERS

Construction of killer toxin fragments by annealing of synthetic oligomers. The DNA oligomers comprise a 5' phosphate group. The sequences of the oligomers, KAC117, KAC118, KAC119, KAC120, KAC121, KAC122, KAC123, KAC124, KAC129, KAC130, KAC131, KAC132, KAC125, KAC126, KAC127, KAC128, and KAC133 are set forth in SEQ ID NOs:24–40, respectively.

Oligomers were diluted to a concentration of 100 picomoles in final volume of 500 $\mu$l with 5 $\mu$l polyA (1 mg/mL) and 50 $\mu$l of 10X ligase buffer. Ligase buffer purchased from New England Biolabs, Beverly, Mass., United States.

|        | pKK    | pKG. | pKGK | pmoles/$\mu$l |
|--------|--------|------|------|---------------|
| KAC117 | 4.8$\mu$L | 4.8  | 4.8  | 20.7          |
| KAC122 | 2.9    | 2.9  | 2.9  | 34.3          |
| KAC118 | 4.5    | 4.5  | 4.5  | 22.1          |
| KAC123 | 5      | 5    | 5.   | 20.0          |
| KAC119 | 3.8    | 3.8  | 3.8  | 26.3          |
| KAC124 | 4.6    | 4.6  | 4.6  | 21.5          |
| KAC120 | 3.5    | 3.5  | 3.5  | 28.4          |
| KAC125 | 4      | 4    | 4    | 24.9          |
| KAC121 | 5.4    | 5.4  | 5.4  | 18.4          |
| KAC126 | 2.1    | 2.1  | 2.1  | 46.6          |
| KAC109 | 1      | 1    | 1    |               |
| KAC127 | 9      | 9    | 9    | 11.1          |
| KAC128 |        | 3.6  |      | 27.8          |
| KAC129 |        | 3.6  |      | 27.6          |
| KAC130 | 3.5    |      |      | 28.8          |
| KAC131 | 4.1    |      |      | 24.4          |
| KAC132 |        |      | 2.2  | 44.3          |
| KAC133 |        |      | 4.4  | 22.9          |

Oligomer mixtures were incubated for two minutes in boiling water. The mixture was cooled to room temperature (~3 hours) with a little ice in bath, which was removed from the heat source.

LIGATION INTO YEAST VECTOR

The following is the ligation mixture used to construct the leader/coding sequences:
  2 $\mu$L of 10X ligation solution with ATP
  2 $\mu$L of a fragment from pHIL-A1 vector digested with EcoRI and phosphotased for a total of 30 ng (plasmid described above)
  1 $\mu$L of T4 DNA ligase for a total of 1 one unit
  q.s. to final volume of 20 $\mu$L with water.
  Either 1 $\mu$L or 5 $\mu$L of the above three oligomer mixtures were used for the ligation.
  Incubated overnight at 4° C.

TRANSFORMATION INTO YEAST HOST

The vectors were transformed into Pichia pastoris yeast host, SMD1163, available from Invitrogen (San Diego, Calif., United States).

Before transformation, 3 mL of YEPD was inoculated with P. pastoris SMD1163. This culture was incubated overnight. Ten microliters of this overnight culture was used to inoculate 100 mL of YEPD.

These cells were grown to an $OD_{650}$ of 0.78. Then, the cells were centrifuged for 5 minutes at 3.5 K. Cell pellets were resuspended in 100 mL sterile water. The cells were centrifuged for 5 minutes at 3.5 K. The cell pellets were resuspended in 8 mL of 0.1 M lithium acetate.

The cells were incubated in the lithium acetate for 30 minutes at 30° C. while shaking. Next, the cells were centrifuged again for 5 minutes in a table top centrifuge and the cell pellets were resuspended in 8 mL of 0.1 M lithium acetate.

Ten microliters of either pKK, pKG, or pKGK, ** pg, was added to 100 $\mu$L of the cells in 0.8 M lithium acetate. The cells and DNA were incubated for 30 minutes at 30° C.

Next, 0.6 mL of 40% PEG 3550, was added to the cells and DNA. The mixture was vortexed, and the mixture was incubated for 60 minutes at 30° C.

Then, the cells were centrifuged for 30 minutes and the cell pellets were resuspended in 60 μL of water. The mixture was plated on histidine minus, yeast minimal media.

Deposit Information

The following materials were deposited with the American Type Culture Collection:

| Name | Deposit Date | Accession No. |
| --- | --- | --- |
| *Escherichia coli* XL1 Blue pHIL-A1 paKT | 26 Sept 1995 | 69903 |

The above materials have been deposited with the American Type Culture Collection, Rockville, Md., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These, deposits are provided merely as convenience to those of skill in the art, and are not an admission that a deposit is required under 35 U.S.C. §112. The sequence of the polynucleotides contained within the deposited materials, as well as the amino acid sequence of the polypeptides encoded thereby, are incorporated herein by reference and are controlling in the event of any conflict with the written description of sequences herein. A license may be required to make, use, or sell the deposited materials, and no such license is granted hereby.

What is claimed:

1. A polynucleotide molecule comprising a first nucleotide sequence that encodes at least a fragment of a leader sequence and a second nucleotide sequence that encodes a polypeptide heterologous to the leader sequence, wherein the leader sequence fragment is sufficient for secretion and comprises an amino acid sequence that comprises at least about 70% sequence identity to the amino acid sequence set forth as amino acid residues 1–48 of SEQ ID NO: 2, wherein the heterologous polypeptide is not naturally contiguous to the leader sequence, and wherein upon expression of the polynucleotide molecule in a host cell suitable for expression thereof, the heterologous polypeptide is produced that is free of additional N-terminal amino acids.

2. The polynucleotide molecule of claim 1, wherein the host cell is an eukaryotic cell.

3. The polynucleotide molecule of claim 2, wherein the eukaryotic cell is a yeast cell.

4. The polynucleotide molecule of claim 3, wherein the yeast cell belongs to a genus that is selected from the genera consisting of Pichia, Saccharomyces, Kluyveromyces, and Hansenula.

5. The polynucleotide of claim 3, wherein the yeast cell is selected from the group consisting of *Pichia pastoris, Saccharomyces cerevisiae, Kluyveromyces lactis,* and *Hansenula polymorpha.*

6. The polynucleotide molecule of claim 1, wherein the host cell is a protease A deficient cell.

7. The polynucleotide molecule of claim 1, wherein the host cell is a protease B deficient cell.

8. The polynucleotide molecule of claim 1, wherein the host cell is a protease A and protease B deficient cell.

9. The polynucleotide molecule of claim 1, wherein the leader sequence comprises a signal peptide sequence and a peptidase cleavage site that comprises dibasic amino acid residues.

10. The polynucleotide molecule of claim 1, wherein the amino acid sequence comprises at least about 80% sequence identity to the leader sequence of *Pichia acaciae* killer toxin.

11. The polynucleotide molecule of claim 1, wherein the amino acid sequence comprises at least about 90% sequence identity to the leader sequence of *Pichia acaciae* killer toxin.

12. The polynucleotide molecule of claim 1, wherein the amino acid sequence comprises at least about 95% sequence identity to the leader sequence of *Pichia acaciae* killer toxin.

13. The polynucleotide of claim 1, wherein the polynucleotide is DNA.

14. The polynucleotide of claim 1, wherein the polynucleotide is RNA.

15. An expression vector comprising the polynucleotide of claim 1, wherein the vector replicates independently or integrates into a host genome.

16. A host cell comprising the polynucleotide of claim 1, wherein the host cell effects transcription and translation of the polynucleotide to produce the heterologous polypeptide.

17. A host cell comprising the vector of claim 15, wherein the host cell effects transcription and translation of the polynucleotide to produce the heterologous polypeptide.

18. A method of producing a polypeptide comprising culturing the host cell of claim 16 and obtaining the polypeptide molecule therefrom.

19. A method of producing the polynucleotide molecule of claim 1, comprising linking together in proper reading frame the first nucleotide sequence and the second nucleotide sequence.

20. A method of producing the vector of claim 15, wherein the vector replicates independently, comprising linking together in proper reading frame a replicon and a polynucleotide molecule, wherein the polynucleotide molecule comprises a first nucleotide sequence that encodes at least a fragment of a leader sequence and a second nucleotide sequence that encodes a polypeptide heterologous to the leader sequence, wherein the leader sequence fragment is sufficient for secretion and comprises an amino acid sequence that comprises at least about 70% sequence identity to the amino acid sequence set forth as amino acid residues 1–48 of SEQ ID NO: 2, wherein the heterologous polypeptide is not naturally contiguous to the leader sequence and wherein upon expression of the polynucleotide molecule in a host cell suitable for expression thereof, the heterologous polypeptide is produced that is free of additional N-terminal amino acids.

21. The host cell of claim 16, wherein the cell is selected from the group consisting of a prokaryotic cell and a eukaryotic cell.

22. The host cell of claim 21, wherein the host cell is a eucaryotic cell and the eucaryotic cell is selected from the group consisting of a yeast cell, an avian cell, an insect call, and a mammalian cell.

23. The host cell of claim 22, wherein the cell is a yeast cell, and the yeast cell is selected from the genera consisting of Pichia, Saccharomyces, and Kluyveromyces.

24. The host cell of claim 23, wherein the yeast cell is selected from the group consisting of *Pichia pastoris, Saccharomyces cerevisiae,* and *Kluyveromyces lactis.*

25. The polynucleotide of claim 1, wherein the heterologous polypeptide is a mammalian polypeptide.

26. The polynucleotide of claim 25, wherein the mammalian polypeptide is a human polypeptide.

27. The polynucleotide of claim 1, wherein the polypeptide is one selected from the group consisting of a hormone, a growth factor, a cytokine, a haematopoietic factor, an immunoglobulin, an enzyme, a repressor, a cell differentiation factor, a binding protein, and a transcription factor.

28. The polynucleotide of claim 1, wherein the polypeptide is one selected from the group consisting of growth hormone, luteinizing hormone, thyroid stimulating hormone, oxytocin, insulin, vasopressin, renin, calcitonin, follicle stimulating hormone, prolactin, insulin-like growth factor (IGF-I, IGF-II), an IGF-binding protein, epidermal growth factor (EGF), platelet derived growth factor (PDGF), keratinocyte growth factor (KGF), fibroblast growth factor (FGF), nerve growth factor (NGF), TGF-beta, vascular endothelial cell growth factor (VEGF), erythropoietin (EPO), colony stimulating factor (CSF), interferon, endorphin, enkaphalin, dynorphin, and active fragments thereof.

29. A method of producing a polypeptide encoded by a polynucleotide comprising (a) transforming a host cell with the polynucleotide, (b) allowing the expression thereof to produce the polypeptide and (c) obtaining the polypeptide therefrom, wherein the polynucleotide molecule comprises a first nucleotide sequence that encodes at least a fragment of a leader sequence and a second nucleotide sequence that encodes a polypeptide heterologous to the leader sequence, wherein the leader sequence fragment is sufficient for secretion and comprises an amino acid sequence that comprises at least about 70% sequence identity to the amino acid sequence set forth as amino acid residues 1–48 of SEQ ID NO: 2, wherein the heterologous polypeptide is not naturally contiguous to the leader sequence, and wherein upon expression of the polynucleotide molecule in a host cell suitable for expression thereof, the heterologous polypeptide is produced that is free of additional N-terminal amino acids.

* * * * *